Jan. 29, 1963 C. T. LARUS ETAL Plant Pat. 2,222
GLADIOLUS PLANT
Filed July 21, 1961
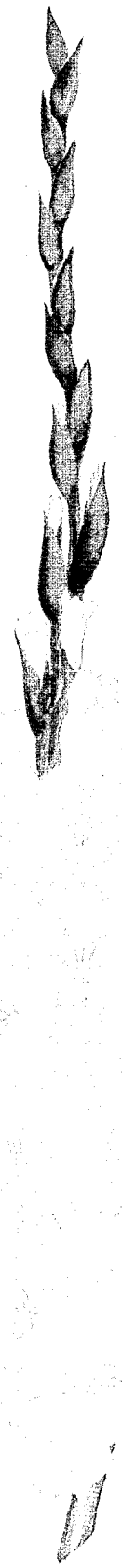
INVENTORS:
Charles T. Larus
John R. Larus
BY: Lamont Johnston
ATTORNEY United States Patent Office Plant Pat. 2,222
Patented Jan. 29, 1963

2,222
GLADIOLUS PLANT

Charles T. Larus, Hartford, and John R. Larus, West Hartford, Conn., assignors to Selected Glads, Inc., New Albany, Ind., a corporation of Tennessee Filed July 21, 1961, Ser. No. 125,884
1 Claim. (Cl. 47—60)

Our present invention relates to a new and improved variety of gladiolus plant and is notable particularly for its rugged vigor, intense ruffling and consistency of performance.

To the best of our knowledge, this new variety is the result of a cross between the varieties Spic and Span (unpatented) and Burma (unpatented); Spic and Span being the seed parent and Burma the pollen parent. Hand cross-pollination was done by us in our field at West Hartford, Connecticut, but no precaution was taken to prevent admixture of other varieties by bees or insects.

The new variety has been asexually reproduced by us in our field at West Hartford, Connecticut, by natural increase from cormels through several generations and its characteristics have proven to be permanently fixed.

The illustration, made a part of this application, shows a single bloom spike of this variety, reduced in size, and is as nearly true to color as it is possible to depict. The illustration shows the intense ruffling, double-row placement, and straightness of stem.

In the following detailed description, color plate references are to the "Horticultural Colour Chart," by the British Colour Council. Where there are other references to color, the ordinary dictionary meanings of the terms are intended.

*The Plant*

Growth: Extremely rugged, the flowering spikes averaging 54–56 inches in height over-all. Prolific propagator.

Blooming: Each spike opens from eight to nine 4 to 4½-inch flowers at one time. Successive blooms open, totalling an average of twenty-two to twenty-four florets to each spike. The variety is a mid-season bloomer, blooming on the average in 85 days from large bulbs.

Stems: Straight and stiff; diameter at base is ½ inch.

Foliage: Healthy green; average leaf is 1¼ inches wide and the plant foliage, excluding the flower spike, is 35 to 36 inches high; slender and upright.

Disease resistance: This variety is very resistant to disease. It has been found resistant to Sclerotina dry rot, Septoria leaf spot and Fusarium yellows, to which some other varieties in our field have been subject, observed when grown as a seedling under irrigation in a black loam soil at West Hartford, Connecticut, under the natural conditions provided by the climate of that area. At the end of the season, it would be found that other varieties and seedlings had succumbed or been badly affected, whereas this variety remained healthy and unaffected.

Corms: Heavy, plump, heavy-husked: average 2½ to 3 inches in diameter from adult plants. Flesh is creased and indented where it comes from the basal scar. Husks have a rose cast: flesh is Indian Yellow $6/_2$.

*The Flower*

Spike: Tall, has twenty-two to twenty-four buds of which three to four are open the first day, following which four to five are open the second day making a total of eight to nine open at once. The flowerhead is 28–30 inches in length.

Bud:

*Size.*—Opening buds are 2 to 2½ inches long.

*Opening.*—Five to six will show color at one time.

Flower:

*Arrangement.*—Flowers are formally placed in a double row on the stem and usually all face forward.

*Size.*—Individual florets measure 4 to 4½ inches in diameter. Upper blooms are progressively smaller.

*Form.*—The florets are somewhat triangular, needle-pointed and heavily ruffled.

*Keeping qualities.*—Keeps and opens well.

Petals:

*Shape.*—Petals are pointed, intensely ruffled, recurved and some are needlepointed.

*Size.*—The outer petals are 2 inches in diameter and the inner petals are 1¼ inches across.

*Aspect.*—Substance is extremely heavy; surface is smooth with some puckering in the throat.

*Fragrance.*—None.

*Color.*—The largest area is Carmine $21/_2$; inner area is $21/_3$; calyx and reverse where petals join is $21/_1$. Blotch is striped or blurred Carmine $21/_2$ on Empire Yellow $603/_3$.

Reproductive organs:

*Stamens.*—Lobelia Blue $41/_1$.

*Pistils.*—Three-pronged, extending about the same distance as the stamen; white hairs.

*Comparisons*

Our new variety resembles Spic and Span (unpatented) more than any other known variety, but differs from it principally as follows:

(1) Our variety is more rugged than Spic and Span.

(2) Our variety is heavier in substance than Spic and Span.

(3) Our variety is more ruffled than Spic and Span.

(4) Our variety is rosier in tone and more flecked than Spic and Span.

(5) Our variety has a darker blotch than Spic and Span.

(6) Our variety is healthier than Spic and Span.

Having thus disclosed our invention, we claim:

The new and distinct variety of gladiolus plant, substantially as herein shown and described, characterized by its robust growth, health, intensely ruffled florets, formal spike and ability to produce several flowering spikes from one bulb.

No references cited.